United States Patent [19]

Pedrazzoli et al.

[11] 4,293,560

[45] Oct. 6, 1981

[54] TALAMPICILLIN 2-METHOXYPHENOXYACETATE AND PHARMACEUTICAL COMPOSITIONS CONTAINING IT

[75] Inventors: Andrea Pedrazzoli, Milan; Sergio Boveri, Monza, both of Italy

[73] Assignee: C M Industries, France

[21] Appl. No.: 161,687

[22] Filed: Jun. 23, 1980

[51] Int. Cl.$^3$ ..................... A61K 31/34; C07D 499/68
[52] U.S. Cl. .................................. 424/271; 260/239.1
[58] Field of Search ...................... 260/239.1; 424/271

[56] References Cited

U.S. PATENT DOCUMENTS 3,534,035 10/1970 Nescio .............................. 260/239.1
3,860,579 1/1975 Ferres et al. ..................... 260/239.1
4,206,218 6/1980 Brown et al. ..................... 260/239.1

*Primary Examiner*—Robert Gerstl
*Assistant Examiner*—Vera C. Clarke
*Attorney, Agent, or Firm*—Ostrolenk, Faber, Gerb & Soffen

[57] ABSTRACT

Talampicillin 2-methoxyphenoxyacetate; a process for its preparation by acid hydrolysis of the metampicillin phthalidyl ester in a biphasic aqueous-organic solvent and treatment of the resulting aqueous phase with an alkali metal salt of the 2-methoxyphenoxyacetic acid; and pharmaceutical compositions containing said talampicillin 2-methoxyphenoxyacetate as an active ingredient.

7 Claims, No Drawings

TALAMPICILLIN 2-METHOXYPHENOXYACETATE AND PHARMACEUTICAL COMPOSITIONS CONTAINING IT

The present invention concerns the 2-methoxyphenoxyacetate of the phthalidyl ester of the 6-[D(—)-α-aminophenylacetamido]penicillanic acid as well as a process for its preparation and pharmaceutical preparations containing said product as active ingredient.

The phtahlidyl ester of the 6-[D(—)-α-aminophenylacetamido]penicillanic acid of the formula

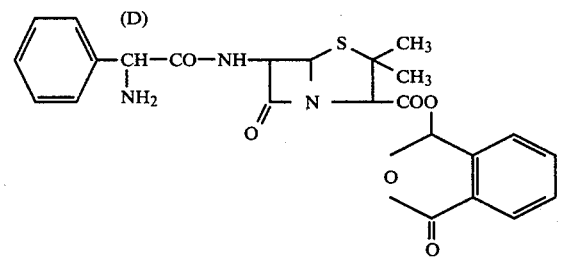

hereinafter referred to as "talampicillin" is a useful ester of the 6-[D(—)-α-aminophenylacetamido]penicillanic acid, hereinafter referred to as "ampicillin" which is well absorbed when administered by oral route in animals and in man thus giving very high blood levels of the parent ampicillin. Talampicillin and its salts, particularly the hydrochloride, are indicated in the British Pat. No. 1364672.

Cilean Pat. No. 31148 discloses the phthalidylester of the 6-[D(—)-α-hydroxymethylaminophenylacetamido]-penicillanic acid of the formula II

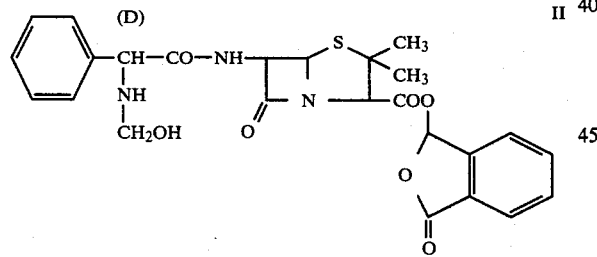

hereinafter referred to as "phthalidyl ester of metampicillin," as well as a process for its preparation and for its optional conversion into talampicillin hydrochloride.

More particularly, the above Cilean patent refers to a process in which an alkali metal or ammonium salt of the 6-[D(—)-αmethyleneaminophenylacetamido]-penicillanic acid of the formula

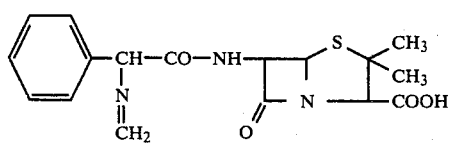

or of the 6[D(—)-α-hydroxymethylaminophenylacetamido]penicillanic acid of the formula

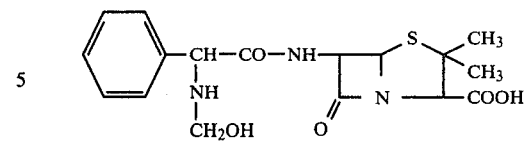

both hereinafter indifferently referred to as "metampicillin," is reacted with a 3-halophthalide and the product thus obtained is hydrolysed in an aqueous-organic biphasic solvent in the presence of hydrochloric acid to obtain talampicillin hydrochloride.

The utility of the phthalidylester of metampicillin resides in that it allows the obtention of a talampicillin hydrochloride of high quality in a practically quantitative yield starting from metampicillin salts or from ampicillin.

European patent application No. 4740 describes and claims the naphthalene 2-sulphonate of talampicillin, hereinafter referred to as "talampicillin napsylate" having a greatly improved taste relative to talampicillin hydrochloride whilst retaining therapeutically effective bioavailability.

It has now been found that by preparing the salt of talampicillin with 2-methoxyphenoxyacetic acid starting from the phthalidylester of metampicillin there is obtained a novel talampicillin salt having an improved absorption with a better bioavailability thus giving higher blood concentrations of the parent ampicillin after oral administration then could be achieved with other talampicillin salts.

Thus, it is an object of the present invention to provide the novel talampicillin 2-methoxyphenoxyacetate having the structural formula

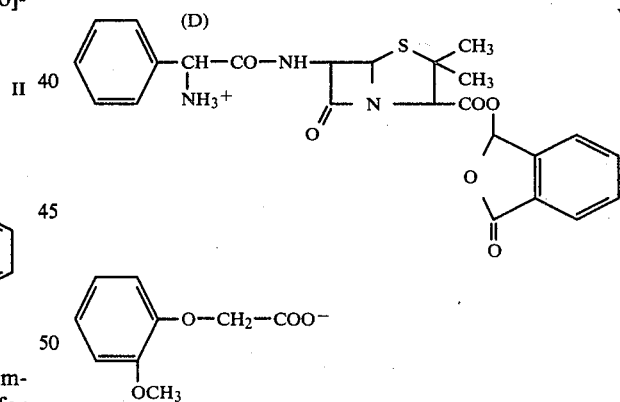

The talampicillin salt V provides a new form of talampicillin having a great stability, a good taste and an enhanced bioavailability.

In respect of talampicillin napsylate described in the European patent application No. 4740, the talampicillin 2-methoxyphenoxyacetate of formula V above has the advantage of an easier preparation because the 2-methoxyphenoxyacetic acid salts are highly soluble in water. On the contrary, particularly the sodium salt of the 2-naphthalene sulphonic acid is soluble only in warm (35° to 40° C.) and in a somewhat high volume of water and often gives a precipitate which must be eliminated by filtration. Furthermore, the talampicillin 2-methoxyphenyxyacetate of the present invention is a white powder which can be isolated from the reaction medium by simple filtration and do not show any problem of storage. From this point of view, the compound of the present invention is particularly advantageous.

In respect of talampicillin hydrochloride, talampicillin 2-methoxyphenoxyacetate has the further advantage of lacking the bitter taste which requires the coating of the tablets and of allowing the preparation of powders for reconstitution into syrups.

Furthermore, in respect of the other talampicillin salts, talampicillin 2-methoxyphenoxyacetate has the advantage of having a better bioavailability thus affording enhanced ampicillin blood levels in animals and in man.

In this connection, talampicillin 2-methoxyphenoxyacetate has been tested in comparison with the following compounds:
sodium ampicillin;
talampicillin hydrochloride;
talampicillin napsylate;
talampicillin 4,4'-methylene-bis-3-hydroxy-2-naphthoate, m.p. 210°-215° C., hereinafter referred to as "talampicillin pamoate," a new talampicillin salt prepared by dissolving talampicillin hydrochloride in water and precipitating by an aqueous solution of sodium pamoate;
talampicillin glutamate, softening point: 100° C., another new talampicillin salt prepared by dissolving talampicillin hydrochloride in water and precipitating by an aqueous solution of glutamic acid.

The compounds have been administered per os to fasting Charles River rats weighing 175 g, at a dose equivalent to 100 mg/kg of acid ampicillin.

The sodium ampicillin and the talampicillin hydrochloride have been administered in aqueous solution; the other talampicillin salts have been administered in aqueous suspension.

At 0.5, 1,2,4 and 6 hours after the administration the animals were sacrificed and their blood was taken from the portal vein.

The antibiotic activity of every pool of plasma has been microbiologically determined on *Sarcina lutea* against a specimen of ampicillin in control rats' plasma.

The ampicillin plasma levels are summarized in Table I. The data refer to an average of three trials carried out on a total of 60 rats per compound. The same table also shows the bioavailability (surface below the curve) of the different talampicillin salts compared with that of ampicillin.

It can be seen from this table that talampicillin 2-methoxyphenoxyacetate gives surprisingly high plasma levels, by far higher than those obtained by the administration of other talampicillin salts, as well as a surprisingly high bioavailability, superior to that of other talampicillin salts.

The comparison between the ampicillin plasma levels obtained after oral administration of talampicillin napsylate and of talampicillin 2-methoxyphenoxyacetate in rats is given in table II.

TABLE I
PLASMA LEVELS AFTER ORAL ADMINISTRATION OF TALAMPICILLIN SALTS IN RAT.

| | Ampicillin plasma level (mcg/ml) | | | | | |
|---|---|---|---|---|---|---|
| Time (h) | Sodium ampicillin | Talampicillin paomate | Talampicillin hydrochloride | Talampicillin napsylate | Talampicillin glutamate | Talampicillin 2-methoxyphenoxyacetate |
| 0.5 | 6.4 | 7.0 | 16.3 | 14.8 | 9.8 | 23.4 |
| 1 | 4.6 | 5.2 | 8.8 | 6.1 | 7.3 | 10.2 |
| 2 | 1.4 | 3.1 | 1.8 | 2.7 | 4.0 | 3.8 |
| 4 | 0.8 | 1.0 | 1.1 | 1.9 | 1.9 | 1.7 |
| 6 | 0.2 | 0.8 | 0.8 | 1.1 | 0.9 | 1.6 |
| | | | Bioavailability | | | |
| Surface below the curve (SBC) | 10.66 | 16.11 | 20.43 | 20.9 | 21.25 | 30 |
| Ratio: SBC talampicillin salt / SBC ampicillin | 1 | 1.5 | 1.92 | 1.96 | 1.99 | 2.81 |

TABLE II

| | mcg/ml ampicillin average ± standard error | |
|---|---|---|
| Time (h) | talampicillin napsylate | talampicillin 2-methoxyphenoxyacetate |
| 0.5 | 14.8 ± 3.4 | 23.4 ± 2.4 |
| 1 | 6.1 ± 1.8 | 10.2 ± 0.9 |
| 2 | 2.7 ± 0.2 | 3.8 ± 1.1 |
| 4 | 1.9 ± 0.6 | 1.7 ± 0.4 |
| 6 | 1.1 ± 0.1 | 1.6 ± 1 |
| SBC* | 20.9 | 30 |

*Ratio $\frac{\text{2-methoxyphenoxyacetate}}{\text{napsylate}} = 1.43$

It appears from this table that talampicillin 2-methoxyphenoxyacetate gives ampicillin plasma levels higher than those given by the napsylate. The difference is statistically significant. The ratio of the surfaces below the curve is clearly favorable to the talampicillin 2-methoxyphenoxyacetate (143%), thus demonstrating a statistically significant better bioavailability of the compound of the present invention in respect of that of the reference compound.

It is another object of the present invention to provide a process for the preparation of talampicillin 2-methoxyphenoxyacetate. Such a process comprises hydrolysing the metampicillin phthalidylester II with an aqueous inorganic or organic acid, preferably with hydrochloric acid in a bi-phasic aqueous-organic solvent and treating the aqueous phase which separates at the end of the hydrolysis with an aqueous solution of an alkali metal salt of the 2-methoxyphenoxyacetic acid.

Thus, the corresponding talampicillin salt separates by precipitation and can be isolated by simple filtration.

According to the process of the present invention, described in the Examples below, the hydrolysis is carried out with hydrochloric acid because this acid is easily available but it is quite evident that one can use another acid giving, at the end of the hydrolysis, a talampicillin salt soluble in water, e.g. hydrobromic, sulphuric or methane sulphonic acid. The utilization of these organic or inorganic acids is included in the scope of the present invention.

The process of the present invention can be carried out on a metampicillin phthalidyl ester II in the pure state or as a raw material at the end of its preparation starting from a metampicillin salt or from ampicillin as described in the Cilean Pat. No. 31148.

It is a further object of the present invention to provide pharmaceutical compositions containing talampicillin 2-methoxyphenoxyacetate as active ingredient in admixture with a pharmaceutical carrier.

The pharmaceutical compositions of the present invention are administered by oral route in solid or liquid dosage unit forms such as tablets, capsules, powders, granules, suspensions, syrups containing the appropriate amount of the active ingredient.

Tablets may contain the active ingredient in admixture with conventional pharmaceutical excipients, e.g. inert diluents such as calcium carbonate, lactose, talc, granulating and disintegrating agent e.g. starch or alginic acid; binding agents, e.g. starch, gelatin or acacia and lubricating agents, e.g. magnesium stearate, stearic acid or talc. The tablets may be uncoated or coated by known techniques.

Capsules may contain the active ingredient alone or admixed with an inert solid diluent e.g. calcium carbonate, calcium phosphate or kaolin.

Granules for reconstitution into a liquid oral preparation can be prepared by using water soluble diluents. The active ingredient is mixed with such an hydrosoluble diluent, such as saccharose, glucose and the like, with a binding agent such as acacia mucilage or a gelatine or methylcellulose solution and the mixture is passed through a sieve to form granules which are then dried. It is advantageous to introduce into the composition a suspending agent such as tragacanth.

Similarly, suspensions, syrups and elixirs may contain the active ingredient in admixture with any of the conventional excipients utilized for the preparation of such compositions, e.g. suspending agents such as methylcellulose, tragacanth and sodium alginate, wetting agents such as lecithin or polyoxyethylene sorbitan and preservatives such as ethyl parahydroxybenzoate.

The liquid preparations are administered in dosage units consisting of a teaspoon of composition, corresponding to 5 ml, containing the calculated amount of active ingredient.

The compositions of the present invention may contain one or more conventional adjuvants, such as sweetening agents, flavoring agents, colouring agents in order to provide an elegant and palatable preparation.

The compositions of the present invention contain from about 20 mg to about 1000 mg of active ingredient per dose unit. Preferred dose units contain 160, 320, 480 or 640 mg of talampicillin 2-methoxyphenoxyacetate corresponding to 125, 250, 375 and, respectively, 500 mg of talampicillin hydrochloride.

The pharmaceutical compositions of the present invention are useful in the treatment of infections in mammals due to pathogenic microorganisms sensitive to ampicillin. The daily dosage may vary from about 80 mg to about 2500 mg divided in three our four administrations, in order to maintain high and constant ampicillin blood levels.

The following examples illustrate the invention without limiting it.

EXAMPLE 1

To a solution of 20.4 g of phthalidyl ester of metampicillin in 100 ml of ethyl acetate there is added a solution of 40 ml of N hydrochloric acid in 120 ml of water. The mixture is maintained under stirring for 45 minutes at room temperature, the organic phase is separated off and the aqueous phase is washed twice with diethyl ether. The aqueous solution is let stand for 20 minutes at 20° C. under reduced pressure, and then it is filtered through asbestos pretreated with hydrochloric acid. To the clear solution thus obtained, there is added, quickly, drop by drop and under stirring a solution of 8 g of 2-methoxyphenoxyacetic acid in 100 ml of water containing 1.76 g of sodium hydroxide. The precipitate which forms is filtered, washed with water and dried on $P_2O_5$ at room temperature and under reduced pressure, to give the talampicillin 2-methoxyphenoxyacetate; m.p. 105°–110° C. (dec.).

EXAMPLE 2

To a suspension of 262 g of anhydrous ampicillin in 1850 ml of dimethylformamide, there is added, at a temperature of 5° C. and under stirring, 62 ml of an aqueous solution of a 40% aqueous solution of formaldehyde, and then, 54 g of anhydrous potassium carbonate. The mixture is stirred for 90 minutes at a temperature from 0° to 5° C., and then it is treated with 160 g of 3-bromophthalide. The reaction mixture is maintained under stirring at 10°–13° C. for further 4 hours, and then it is poured into 5 liters of water ice. The precipitate which forms is filtered, washed with 1000 ml of cold water and dissolved in 1700 ml of ethyl acetate. The residual water is eliminated, the organic solution is treated with 760 ml of N hydrochloric acid and 2500 ml of water and the resulting mixture is stirred for 45 minutes at room temperature. The aqueous layer is separated off, then it is washed once again with 200 ml of diethyl ether, maintained under reduced pressure at 20° C. for 20 minutes, and then it is filtered on asbestos pretreated with hydrochloric acid. To the clear solution so obtained, 3500 ml about, there is added, drop by drop for about 10 minutes, under stirring, a solution of 145 g of 2-methoxyphenoxyacetic acid in 1800 ml of water containing 32 g of sodium hydroxide. The precipitate which forms is left stirring for further 5 minutes, and then it is washed with 500 ml of water and dried on $P_2O_5$ at a temperature of 25° to 30° C. under reduced pressure. The talampicillin 2-methoxyphenoxyacetate is so obtained, and is identical to the product described in Example 1.

EXAMPLE 3

A composition for tablets is prepared having the following formula:

| | |
|---|---|
| talampicillin 2-methoxyphenoxyacetate | 480 mg |
| glycine | 130 mg |
| microgranular cellulose | 70 mg |
| precipitated silica | 19 mg |
| carboxymethyl starch | 35 mg |
| magnesium stearate | 13 mg |
| talc | 13 mg |

The calculated amounts of the ingredients are mixed for 30 minutes, then dry granulated and passed through a 1.6 mm-mesh sieve. Then the mixture is compressed by using a die having the shape of a little stick.

Tablets each weighing 760 mg and each containing 480 mg of active ingredient are so obtained.

Analogously tablets are prepared each containing 640 mg of talampicillin 2-methoxyphenoxyacetate.

EXAMPLE 4

Tablets are prepared following the same procedure as described in Example 3. The tablets so obtained are coated with a suspension of dibutyl phthalate, butyl polymethacrylate and dimethylaminoethyl, polyethylene glycol 1500, precipitated silica, titanium dioxide and talc in a mixture acetone/isopropanol 1:1, having a dry residue of 10% about. Tablets coated each weighing 780 mg and each containing 480 mg of talampicillin 2-methoxyphenoxycetate are so obtained.

EXAMPLE 5

Granules for reconstitution into a liquid oral preparation having the following composition are prepared:

| | |
|---|---|
| talampicillin 2-methoxyphenoxyacetate | 3.60 g |
| saccharose | 50.00 g |
| sodium carboxyethyl cellulose | 0.80 g |
| citric acid | 0.10 g |
| trisodium citrate | 0.90 g |
| sodium benzoate | 0.25 g |
| saccharin sodium | 0.15 g |
| flavoring | 0.50 g |

The volume of the granules so obtained is brought up to 100 ml with water for syrups. A unit dose of 5 ml of extemporaneous syrup so obtained contains 160 mg of talampicillin 2-methoxyphenoxyacetate.

The mixture in granular form is prepared by pulverizing the calculated amounts of all the components, except for the saccharose, and by mixing the powder so obtained with the saccharose until homogeneous granules are obtained.

EXAMPLE 6

Following the same procedure as described in Example 5 granules for reconstitution into a liquid oral preparation, having the following composition, are prepared:

| | |
|---|---|
| talampicillin 2-methoxyphenoxyacetate | 7.20 |
| saccharose | 46.40 g |
| sodium carboxymethylcellulose | 0.90 g |
| citric acid | 0.10 g |
| trisodium citrate | 0.90 g |
| sodium benzoate | 0.25 g |
| saccharin sodium | 0.15 g |
| flavoring | 0.50 g |

A unit dose of 5 ml of extemporaneous syrup so obtained contains 320 mg of talampicillin 2-methoxyphenoxyacetate.

EXAMPLE 7

Following the same procedure as described in Example 5, granules for reconstitution into a liquid oral preparation, having the following composition, are prepared:

| | |
|---|---|
| talampicillin 2-methoxyphenoxyacetate | 9.60 g |
| saccharose | 44.00 g |
| sodium carboxymethylcellulose | 1.00 g |
| citric acid | 0.10 g |
| trisodium citrate | 0.90 g |
| sodium benzoate | 0.25 g |
| saccharin sodium | 0.15 g |
| flavoring | 0.50 g |

A unit dose of 5 ml of extemporaneous syrup so obtained contains 480 mg of talampicillin 2-methoxyphenoxyacetate.

What is claimed is:

1. The 2-methoxyphenoxyacetate acid salt of the phthalidyl ester of the 6-[D(−)-α-aminophenylacetamido]penicillanic acid of the formula

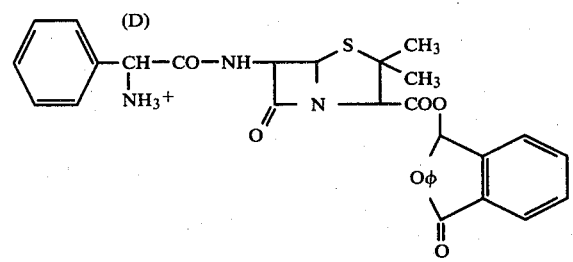

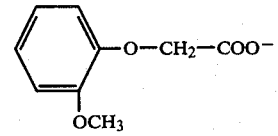

2. A pharmaceutical composition in unit dosage form, for use in the treatment of infections sensitive to ampicillin, comprising about 20–1000 mg per dosage unit of the 2-methoxyphenoxyacetate of the phthalidyl ester of 6-[D(−)-α-aminophenylacetamido]penicillanic acid in admixture with a pharmaceutical carrier.

3. A pharmaceutical composition as claimed in claim 2 which is in form of granules for the reconstitution into a liquid oral preparation.

4. A pharmaceutical composition as claimed in claim 2 or 3 containing 160 mg 2-methoxyphenoxyacetate of the phthalidyl ester of 6-[D(−)-α-aminophenylacetamido]penicillanic acid per dosage unit.

5. A pharmaceutical composition as claimed in claim 2 or 3 containing 320 mg of 2-methoxyphenoxyacetate of the phthalidyl ester of 6-[D(−)-α-aminophenylacetamido]penicillanic acid per dosage unit.

6. A pharmaceutical composition as claimed in claim 2 or 3 containing 480 mg of 2-methoxyphenoxyacetate of the phthalidyl ester of 6-[D(−)-α-aminophenylacetamido]penicillanic acid per dosage unit.

7. A pharmaceutical composition as claimed in claim 2 or 3 containing 640 mg of 2-methoxyphenoxyacetate of the phthalidyl ester of 6-[D(−)-α-aminophenylacetamido]penicillanic acid per dosage unit.

* * * * *